(12) United States Patent
Forrer et al.

(10) Patent No.: US 8,608,805 B2
(45) Date of Patent: Dec. 17, 2013

(54) INSERT AND SHELL OF A JOINT BALL RECEPTACLE

(75) Inventors: Michael Forrer, Seuzach (CH); Nicole Gronau, Winterthur (CH); Stefan Boss, Widen (CH); Ines Baum, Constance (DE)

(73) Assignee: Zimmer GmbH, Winterthur (CH)

( * ) Notice: Subject to any disclaimer, the term of this patent is extended or adjusted under 35 U.S.C. 154(b) by 205 days.

(21) Appl. No.: 12/066,948

(22) PCT Filed: Sep. 15, 2006

(86) PCT No.: PCT/EP2006/066410
§ 371 (c)(1),
(2), (4) Date: May 5, 2008

(87) PCT Pub. No.: WO2007/031575
PCT Pub. Date: Mar. 22, 2007

(65) Prior Publication Data
US 2008/0228281 A1    Sep. 18, 2008

(30) Foreign Application Priority Data

Sep. 16, 2005  (EP) ..................................... 05020296
Dec. 1, 2005   (CH) ..................................... 1907/05

(51) Int. Cl.
*A61F 2/40*   (2006.01)
(52) U.S. Cl.
USPC ..................................................... 623/19.12
(58) Field of Classification Search
USPC .......... 623/19.11–19.14, 22.11, 22.15, 22.17, 623/22.19–22.21, 22.24, 22.26, 22.28–22.3, 623/22.4, 22.22–22.23, 23.39, 23.4, 23.41
IPC ......................................................... A61F 2/40
See application file for complete search history.

(56) References Cited

U.S. PATENT DOCUMENTS

| 3,815,157 A | 6/1974 | Skorecki et al. |
| 3,842,442 A | 10/1974 | Kolbel |

(Continued)

FOREIGN PATENT DOCUMENTS

| AU | 714659 | 10/1996 |
| CA | 2216955 | 2/2004 |

(Continued)

OTHER PUBLICATIONS

International Search Report mailed Feb. 1, 2007 in related application No. PCT/EP2006/066410.

(Continued)

*Primary Examiner* — David Isabella
*Assistant Examiner* — Marcia Hoffman
(74) *Attorney, Agent, or Firm* — Schwegman, Lundberg & Woessner P.A.

(57) ABSTRACT

An insert (11) of a joint ball receptacle of a prosthetic shoulder joint according to the invention has a first side (I) with a depression (15) for receiving a joint ball, and a second side (II) which is provided and formed for being received in a shell (13) of the joint ball receptacle. According to the invention, a snap action mechanism (19) which extends around a central axis (17) of the insert (11) is arranged on the second side (II), which snap-action mechanism (19) has, as seen from the second side (II), and together with a collar (21), an undercut (23) which extends around the central axis (17), in such a way that the collar (21) can engage with elastic deformation behind a correspondingly formed mating element (25) of the shell (13), wherein the snap-action mechanism (19) is discontinuous in the peripheral direction of the insert (11) at at least one point (31); according to the invention, the insert (11) has a cylindrical guide region (27) at the outer periphery in the region provided for being received in the shell (13).

28 Claims, 12 Drawing Sheets

(56) References Cited

U.S. PATENT DOCUMENTS

| | | | |
|---|---|---|---|
| 3,869,730 | A | 3/1975 | Skobel |
| 3,916,451 | A | 11/1975 | Buechel et al. |
| 3,978,528 | A | 9/1976 | Crep |
| 4,030,143 | A | 6/1977 | Elloy et al. |
| 4,040,131 | A | 8/1977 | Gristina |
| 4,206,517 | A | 6/1980 | Pappas et al. |
| 4,608,052 | A | 8/1986 | Van Kampen et al. |
| 4,645,450 | A | 2/1987 | West |
| 4,664,668 | A | 5/1987 | Beck et al. |
| 4,693,723 | A | 9/1987 | Gabard |
| 4,778,469 | A | 10/1988 | Lin et al. |
| 4,784,663 | A * | 11/1988 | Kenna ................. 623/22.29 |
| 4,863,474 | A | 9/1989 | Brown et al. |
| 4,919,669 | A | 4/1990 | Lannelongue |
| 4,963,155 | A | 10/1990 | Lazzeri et al. |
| 4,964,865 | A | 10/1990 | Burkhead et al. |
| 5,007,931 | A | 4/1991 | Smith |
| 5,080,673 | A | 1/1992 | Burkhead et al. |
| 5,108,447 | A * | 4/1992 | Zeiler et al. ................. 623/22.14 |
| 5,133,764 | A | 7/1992 | Pappas et al. |
| 5,275,601 | A | 1/1994 | Gogolewski et al. |
| 5,314,479 | A | 5/1994 | Rockwood, Jr. et al. |
| 5,326,354 | A | 7/1994 | Kwarteng |
| 5,358,526 | A | 10/1994 | Tornier |
| 5,429,639 | A | 7/1995 | Judet |
| 5,462,563 | A | 10/1995 | Shearer et al. |
| 5,520,690 | A | 5/1996 | Errico et al. |
| 5,531,746 | A | 7/1996 | Errico et al. |
| 5,534,027 | A | 7/1996 | Hodorek |
| 5,549,682 | A | 8/1996 | Roy |
| 5,571,202 | A | 11/1996 | Mathys, Sr. et al. |
| 5,607,426 | A | 3/1997 | Ralph et al. |
| 5,643,265 | A | 7/1997 | Errico et al. |
| 5,647,873 | A | 7/1997 | Errico et al. |
| 5,669,911 | A | 9/1997 | Errico et al. |
| 5,690,630 | A | 11/1997 | Errico et al. |
| 5,702,457 | A | 12/1997 | Walch et al. |
| 5,702,486 | A | 12/1997 | Craig et al. |
| 5,723,018 | A | 3/1998 | Cyprien et al. |
| 5,725,588 | A | 3/1998 | Errico et al. |
| 5,817,094 | A | 10/1998 | Errico et al. |
| 5,876,402 | A | 3/1999 | Errico et al. |
| 5,888,204 | A | 3/1999 | Ralph et al. |
| 6,045,582 | A | 4/2000 | Prybyla |
| 6,139,550 | A | 10/2000 | Michelson |
| 6,197,063 | B1 | 3/2001 | Dews |
| 6,206,925 | B1 | 3/2001 | Tornie |
| 6,228,120 | B1 | 5/2001 | Leonard et al. |
| 6,283,999 | B1 | 9/2001 | Rockwood, Jr. |
| 6,334,874 | B1 | 1/2002 | Tornier et al. |
| RE37,665 | E | 4/2002 | Ralph et al. |
| 6,368,352 | B1 | 4/2002 | Camino et al. |
| 6,398,812 | B1 | 6/2002 | Masini |
| 6,520,994 | B2 | 2/2003 | Nogarin |
| 6,524,342 | B1 | 2/2003 | Muhlhausler et al. |
| 6,558,387 | B2 | 5/2003 | Errico et al. |
| 6,558,425 | B2 | 5/2003 | Rockwood, Jr. |
| 6,589,282 | B2 | 7/2003 | Pearl |
| 6,620,197 | B2 | 9/2003 | Maroney et al. |
| 6,626,946 | B1 | 9/2003 | Walch et al. |
| 6,673,114 | B2 | 1/2004 | Hartdegen et al. |
| 6,679,916 | B1 | 1/2004 | Frankle et al. |
| 6,719,799 | B1 | 4/2004 | Kropf |
| 6,736,851 | B2 | 5/2004 | Maroney et al. |
| 6,736,852 | B2 | 5/2004 | Callaway et al. |
| 6,749,637 | B1 | 6/2004 | Bahler |
| 6,761,740 | B2 | 7/2004 | Tornier |
| 6,776,799 | B2 | 8/2004 | Ball et al. |
| 6,780,190 | B2 | 8/2004 | Maroney |
| 6,790,234 | B1 | 9/2004 | Frankle |
| 6,863,690 | B2 | 3/2005 | Ball et al. |
| 6,887,277 | B2 | 5/2005 | Rauscher et al. |
| 6,899,736 | B1 | 5/2005 | Rauscher et al. |
| 6,942,699 | B2 | 9/2005 | Stone et al. |
| 6,953,478 | B2 | 10/2005 | Bouttens et al. |
| 6,969,406 | B2 | 11/2005 | Tornier |
| 6,986,790 | B2 | 1/2006 | Ball et al. |
| 7,011,686 | B2 | 3/2006 | Ball et al. |
| 7,169,184 | B2 | 1/2007 | Dall Pria |
| 7,175,663 | B1 | 2/2007 | Stone |
| 7,854,768 | B2 | 12/2010 | Wiley et al. |
| 2001/0011193 | A1 | 8/2001 | Nogarin |
| 2001/0037152 | A1 | 11/2001 | Rockwood, Jr. |
| 2001/0041940 | A1 | 11/2001 | Pearl |
| 2001/0049561 | A1 | 12/2001 | Dews et al. |
| 2001/0053935 | A1 | 12/2001 | Hartdegen et al. |
| 2002/0016634 | A1 | 2/2002 | Maroney et al. |
| 2002/0095215 | A1 | 7/2002 | Camino et al. |
| 2002/0099445 | A1 | 7/2002 | Maroney et al. |
| 2002/0120339 | A1 | 8/2002 | Callaway et al. |
| 2002/0151982 | A1 | 10/2002 | Masini |
| 2003/0014119 | A1 | 1/2003 | Capon et al. |
| 2003/0028253 | A1 | 2/2003 | Stone et al. |
| 2003/0097183 | A1 | 5/2003 | Rauscher et al. |
| 2003/0100952 | A1 | 5/2003 | Rockwood, Jr. et al. |
| 2003/0114933 | A1 | 6/2003 | Bouttens et al. |
| 2003/0149485 | A1 | 8/2003 | Tornier |
| 2004/0002765 | A1 | 1/2004 | Maroney et al. |
| 2004/0034431 | A1 | 2/2004 | Maroney et al. |
| 2004/0054420 | A1 | 3/2004 | Meswania |
| 2004/0064187 | A1 | 4/2004 | Ball et al. |
| 2004/0064188 | A1 | 4/2004 | Ball et al. |
| 2004/0064190 | A1 | 4/2004 | Ball et al. |
| 2004/0094187 | A1 | 5/2004 | Lee |
| 2004/0143335 | A1 | 7/2004 | Dews et al. |
| 2004/0153161 | A1 | 8/2004 | Stone et al. |
| 2004/0167629 | A1 | 8/2004 | Geremakis et al. |
| 2004/0181286 | A1 | 9/2004 | Michelson |
| 2004/0186579 | A1 | 9/2004 | Callaway et al. |
| 2004/0220673 | A1 | 11/2004 | Pria |
| 2004/0220674 | A1 | 11/2004 | Pria |
| 2004/0225367 | A1 | 11/2004 | Glien et al. |
| 2004/0230311 | A1 | 11/2004 | Cyprien et al. |
| 2004/0267370 | A1 | 12/2004 | Ondria |
| 2005/0033443 | A1 | 2/2005 | Blatter et al. |
| 2005/0065612 | A1 | 3/2005 | Winslow |
| 2005/0071014 | A1 | 3/2005 | Barnett et al. |
| 2005/0107882 | A1 | 5/2005 | Stone et al. |
| 2005/0113931 | A1 | 5/2005 | Horber |
| 2005/0143829 | A1 | 6/2005 | Ondria et al. |
| 2005/0165490 | A1 | 7/2005 | Tornier |
| 2005/0177241 | A1 | 8/2005 | Angibaud et al. |
| 2005/0197708 | A1 | 9/2005 | Stone et al. |
| 2005/0251263 | A1 | 11/2005 | Forrer et al. |
| 2005/0256583 | A1 | 11/2005 | Bouttens et al. |
| 2005/0261775 | A1 | 11/2005 | Baum et al. |
| 2005/0278030 | A1 | 12/2005 | Tornier et al. |
| 2005/0278031 | A1 | 12/2005 | Tornier et al. |
| 2005/0278033 | A1 | 12/2005 | Tornier et al. |
| 2005/0288681 | A1 | 12/2005 | Klotz et al. |
| 2005/0288791 | A1 | 12/2005 | Tornier et al. |
| 2006/0009852 | A1 | 1/2006 | Winslow et al. |
| 2006/0020344 | A1 | 1/2006 | Shultz et al. |
| 2006/0036328 | A1 | 2/2006 | Parrott et al. |
| 2006/0069445 | A1 | 3/2006 | Ondria et al. |
| 2007/0173945 | A1 | 7/2007 | Wiley |
| 2008/0294268 | A1 | 11/2008 | Baum et al. |

FOREIGN PATENT DOCUMENTS

| | | |
|---|---|---|
| DE | 3914809 A1 | 11/1990 |
| DE | 4128259 A1 | 3/1993 |
| DE | 19606057 C2 | 8/1997 |
| DE | 29918669 U1 | 12/1999 |
| DE | 29918589 U1 | 3/2000 |
| EP | 0190093 A1 | 8/1986 |
| EP | 0337513 B1 | 10/1989 |
| EP | 0350435 A1 | 1/1990 |
| EP | 0530585 B1 | 3/1993 |
| EP | 0621018 A1 | 10/1994 |
| EP | 0631497 B1 | 1/1995 |
| EP | 0679375 A1 | 11/1995 |
| EP | 0853928 A1 * | 12/1997 |
| EP | 0853928 A1 | 7/1998 |

(56) References Cited

FOREIGN PATENT DOCUMENTS

| | | |
|---|---|---|
| EP | 0927548 A2 | 7/1999 |
| EP | 1004283 A2 | 5/2000 |
| EP | 1093777 A2 | 4/2001 |
| EP | 1125565 A2 | 8/2001 |
| EP | 1216668 A2 | 6/2002 |
| EP | 1314407 A1 | 5/2003 |
| EP | 0828459 B1 | 9/2003 |
| EP | 1415621 A2 | 5/2004 |
| EP | 1472999 A1 | 11/2004 |
| EP | 1527757 A1 | 5/2005 |
| EP | 1543801 A1 | 6/2005 |
| EP | 1364623 B1 | 10/2005 |
| EP | 1591084 A1 | 11/2005 |
| EP | 1598034 A1 | 11/2005 |
| EP | 1393697 B1 | 2/2006 |
| FR | 2617040 A1 | 12/1988 |
| FR | 2652498 A1 | 4/1991 |
| FR | 2674122 A1 | 9/1992 |
| FR | 2699400 A1 | 6/1994 |
| FR | 2704747 A1 | 11/1994 |
| FR | 2825263 A1 | 12/2002 |
| GB | 2069338 A | 8/1981 |
| GB | 2268408 A | 1/1994 |
| GB | 2405346 A | 3/2005 |
| JP | 11503351 T | 3/1999 |
| JP | 2004113804 A | 4/2004 |
| JP | 2004121850 A | 4/2004 |
| WO | WO96/32071 A1 | 10/1996 |
| WO | WO2005/032430 A1 | 4/2005 |
| WO | WO2007/082925 A1 | 7/2007 |

OTHER PUBLICATIONS

Search Report mailed Aug. 17, 2006 in related application No. CH01907/05.
Surgical Technique, Delta CTA Reverse Shoulder System—DuPuy (delta) 2004.
Article—Initial Glenoid Component Fixation in "Reverse"Total Shoulder Arthroplasty: A Biomechanical Evaluation, Harman et al., In press JSES 2005 (harman).
Article—The Reverse Shoulder Prosthesis for Glenohumeral Arthritis Associated with Severe Rotator Cuff Deficiency, Mark Frankle, MD et al., 2005 by the Journal of Bone and Joint Surgery, Incorporated, pp. 1697-1705 (Frankle).
Surgical Technique—Anatomical Shoulder System, 36 pages, 06-006-070-12 Rev. 1 5ML, 2004 Zimmer, Inc. (Anatomical_Shoulder_System_Surgical_Technique_06-006-070-12_Rev.pdf).
Website—www.tornier-us.com/product_shldr_aqu.htm#—last accessed Feb. 27, 2006 (tornier).
Webpage and Patient Information—Baylor College of Medicine, Reverse Total Shoulder Arthroplasty, Jeffrey E. Budoff, M.D., Department of Orthopaedic Surgery, last modified Mar. 30, 2006: http://www.waybackmachine.org/web/20060915050157/http://www.bcm.edu/ortho/md/budoff/patienteducation/reversetotalshoulderarthroplasty.htm (Budoff2).
Article from Medscape Today, WebMD, Shoulder Arthroplasty, Andrew H. Schmidt, M.D. accessed Feb. 28, 2007 (schmidt).

\* cited by examiner

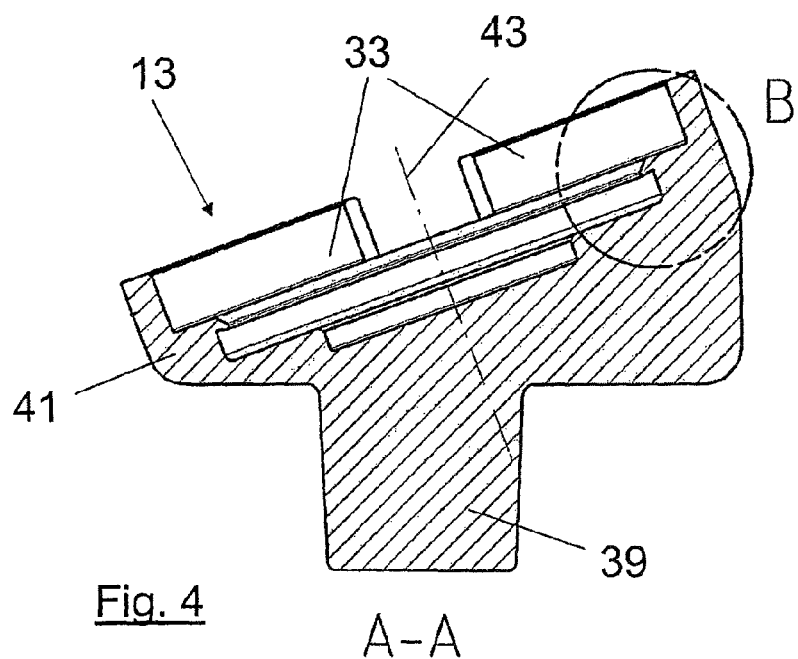
Fig. 4   A-A
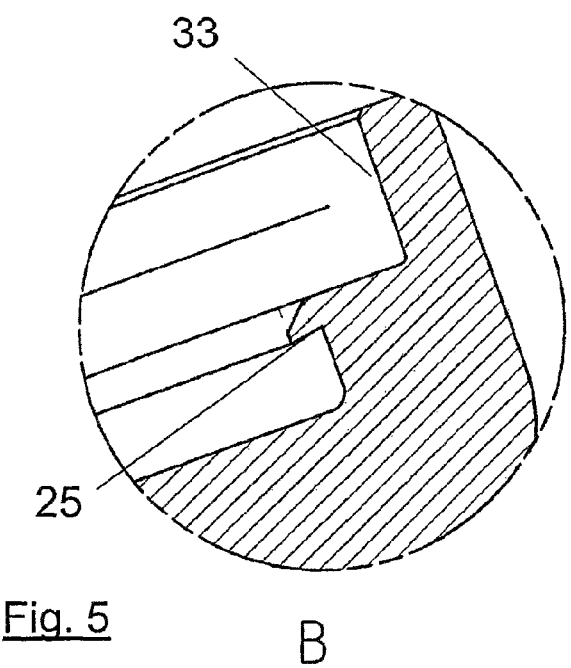
Fig. 5   B

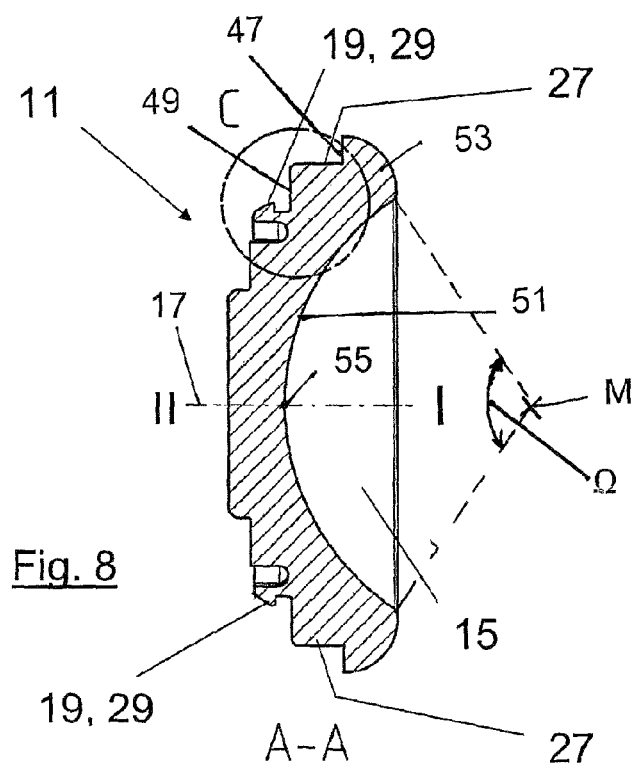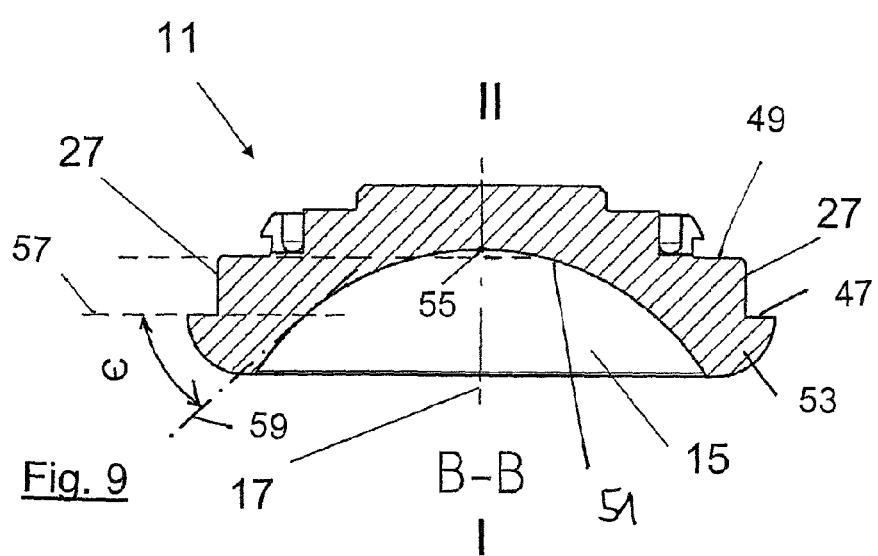

E-E

INSERT AND SHELL OF A JOINT BALL RECEPTACLE

CROSS REFERENCE TO RELATED APPLICATION

This application is a U.S. National Phase Patent Application based on International Application Serial No. PCT/EP2006/066410 filed Sep. 15, 2006, the disclosure of which is hereby explicitly incorporated by reference herein.

SUMMARY

The invention relates to an insert of a joint ball mount of, for example, a shoulder joint prosthesis. In exemplary forms thereof, the invention furthermore relates to a shell of a joint ball mount of a shoulder joint prosthesis for use with such an insert, to a joint ball mount of a shoulder joint prosthesis consisting of such an insert and such a shell and also to a complete shoulder joint prosthesis.

With shoulder joints, the selection of the suitable implant and the manner of the implantation decisively depends on the condition in which the involved bones are, with the condition of the muscles, in particular of the rotator cuff, also playing a role. With the shoulder joint, the condition of the shoulder blade is particularly important, and above all in this connection the joint socket, the glenoid, which cooperates with the head of the upper arm, the humerus in the healthy joint. The necessity of a part replacement or complete replacement of the shoulder joint can be present for various reasons. Typical causes are, for example, advanced wear of the joint surfaces or fractures, e.g. due to an accident. Depending on the type and degree of damage, a so-called inverse prosthesis configuration can also be indicated in which the artificial joint ball and the artificial joint mount are swapped over with respect to their positions in a natural joint.

Before possible embodiments of the joint ball mount proposed here are presented with reference to FIGS. 2 to 15, an introductory overview will first be given with reference to FIGS. 1a; , 1b and 1c, The bony structure of the shoulder joint consists of the head of the upper arm bone E and of the joint socket B of the shoulder blade A. In addition, two bone projections of the shoulder blade A, namely the acromion C and the coracoid D, are important for the function of the shoulder joint. These bone projections, together with a ligament, not shown, connecting them, form the so-called "ceiling" of the shoulder which has an arch-like shape and prevents an upward migration of the head of the upper arm from the joint socket. FIG. 1 a shows a so-called anatomical configuration in which the prosthesis reproduces the shoulder joint in its natural structure, i.e. the humerus E is provided with an artificial joint head 116 and the shoulder blade A is provided with an artificial joint ball mount or joint socket 114. The anchorage of the joint socket 114 at the shoulder blade A, more precisely at the correspondingly prepared glenoid B, takes place via screws 114a in the example shown. The anchorage of the artificial joint head 116 at the humerus E takes place by means of a shaft 112 which can have different types of design.

FIG. 1b shows a so-called inverse configuration in which the artificial joint head and the artificial joint socket 114' have been swapped over with respect to their positions in the natural shoulder joint. The joint head is here formed by an artificial joint part which includes a base platform 111 and a ball component 117 firmly connected to the platform 111. The anchorage of the platform 111 at the shoulder blade A, more precisely at the correspondingly prepared glenoid B, takes place in the example shown via a spigot 119 only indicated schematically of the platform 111 and by means of screws 123 for which corresponding screw mounts are provided in the platform 111. Whereas the platform 111 therefore supports the artificial ball component 117 here, the artificial joint socket 114', which forms the ball joint mount, is anchored to the humerus E by means of a shaft 112.

It is known to make joint ball mounts with a shell to be anchored in the bone and an insert to be fastened therein. It is known to make the shell from metal and the insert, which has a recess, for example, for the reception of a joint ball, from plastic. It is known, for example, in accordance with FIG. 1c for the anchorage of an insert in a shell to provide the inner contour of the shell 13 with an undercut and to provide the insert 11 with a peripherally formed and radially outwardly extending collar such that an undercut element is formed which extends in the peripheral direction, extends radially outwardly and is hook-shaped in cross-section. The element can be brought into engagement with the undercut of the shell 13 by elastic deformation, and indeed such that the insert 11 is anchored in the shell 13, as FIG. 1c shows.

With a joint ball mount of the kind set forth here, the collar of the snap-action mechanism is interrupted at at least one point of its periphery. This has the effect that the collar can be deformed more pronouncedly on the introduction of the insert into a shell, which is then expressed in a larger restoring movement of the undercut after the complete introduction of the insert. Due to this larger restoring movement, the undercut can engage behind the corresponding counter-element in the shell to a comparatively large degree or with a relatively large "depth". A good and large-area shape matching can thus ultimately be achieved between the insert and the shell or between the undercut of the insert and the counter-element of the shell. The insert is furthermore provided with a cylindrical guide region. The insert can be combined with a shell in accordance with one of the claims directed to a shell. In this manner, a largely full surface contact of the outer side of the cylindrical guide region of the insert at the inner side of the cylindrical inner guide region of the shell is obtained when the insert is coupled to the shell. The cylindrical guide region takes over a guidance function and/or centering function of the insert in the shell. The function of the coupling of insert and shell achievable with the snap-action mechanism is in particular separate from the function of the guidance and/or centering of the insert. An insert for the joint ball mount of a shoulder prosthesis has become known for GB 2,405,346 which has a snap-action mechanism at its axial end and furthermore has a cylindrical guide region.

BRIEF DESCRIPTION OF THE DRAWINGS

FIG. 4 is a sectional view of the prosthetic shell of FIG. 2;

FIG. 5 is a partial detailed view of the prosthetic shell of FIG. 2;

FIG. 8 is a sectional view of the insert of FIG. 6 taken along line A-A of FIG. 7;

FIG. 9 is a sectional view of the insert of FIG. 6 taken along line B-B of FIG. 7;

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

An embodiment is shown in the FIGS. 2 to 11. A further embodiment is shown in the FIGS. 12 to 15.

Figure 12:
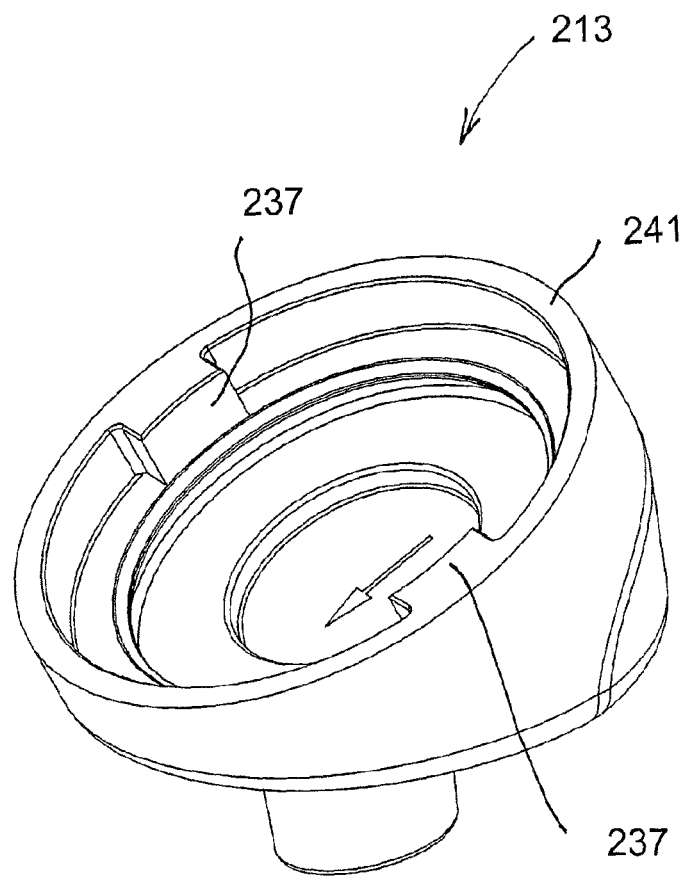
FIG. 12 is a perspective view of an alternative embodiment prosthetic shell.
Figure 13:
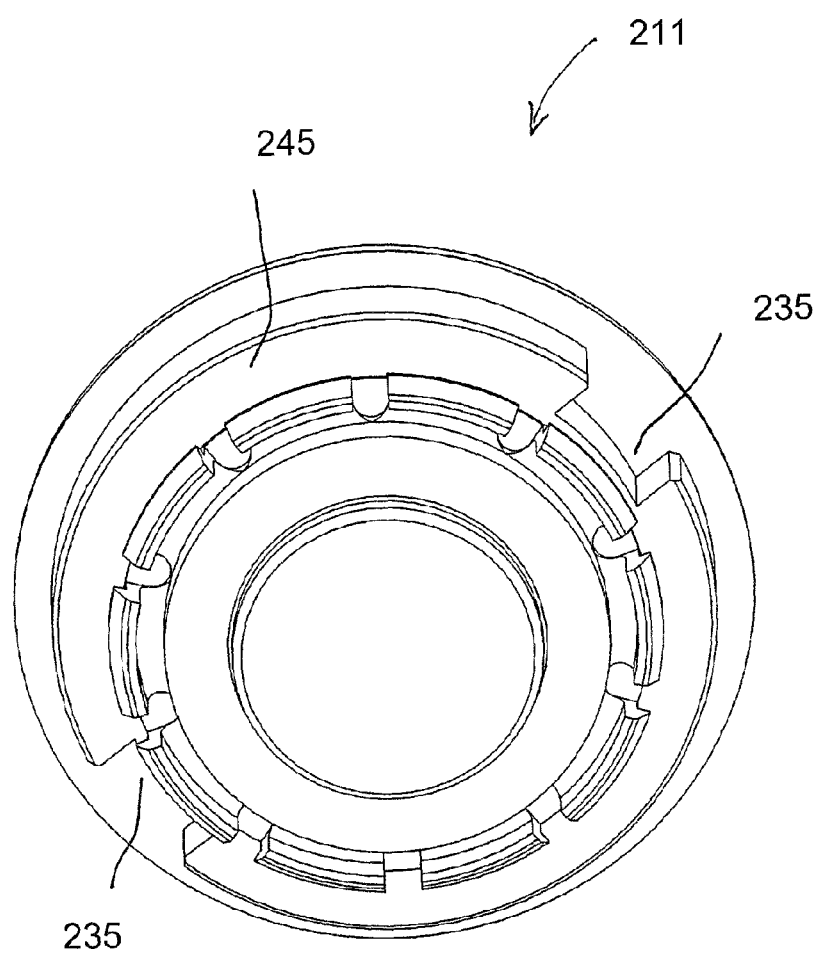
FIG. 13 is a perspective view of an alternative embodiment insert adapted for cooperation with the prosthetic shell of FIG. 12.
Figure 14:
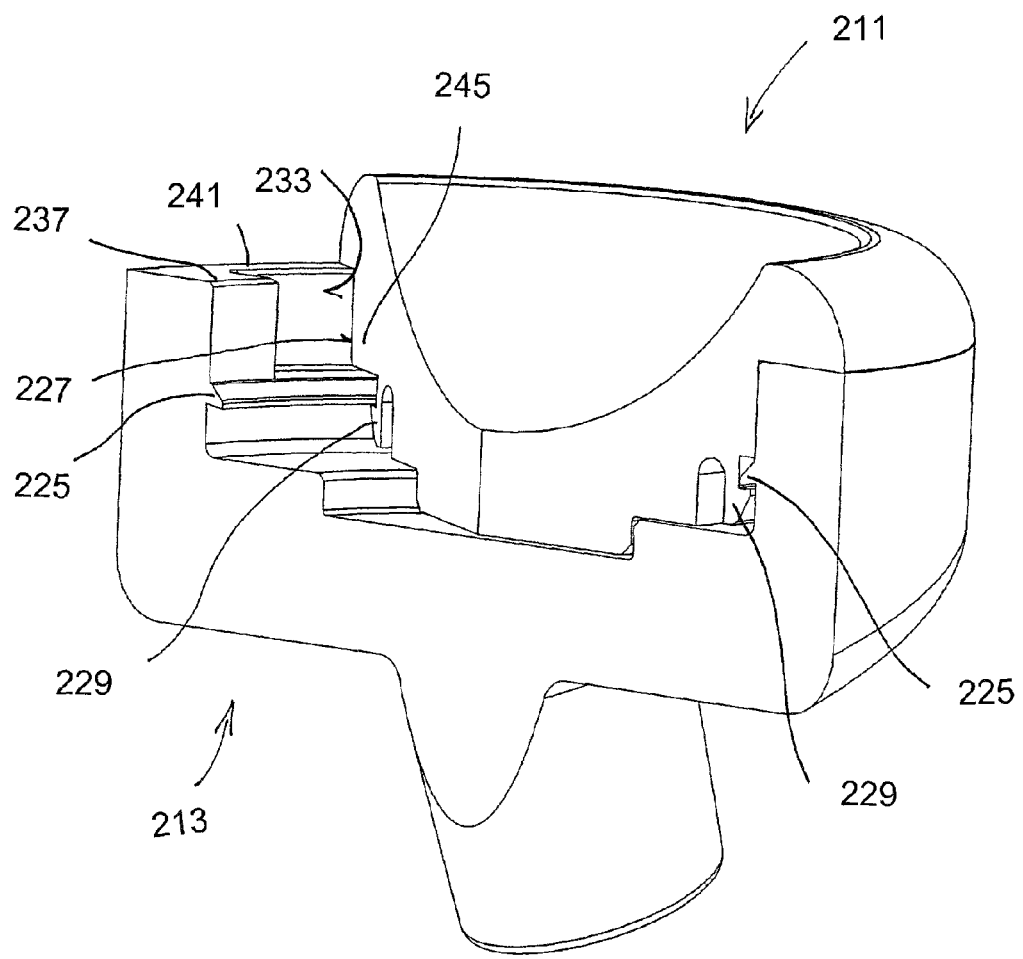
FIGS. 14 and 15 are sectional views illustrating securement of the insert illustrated in FIG. 13 in the prosthetic shell illustrated in FIG. 12.
Figure 15:
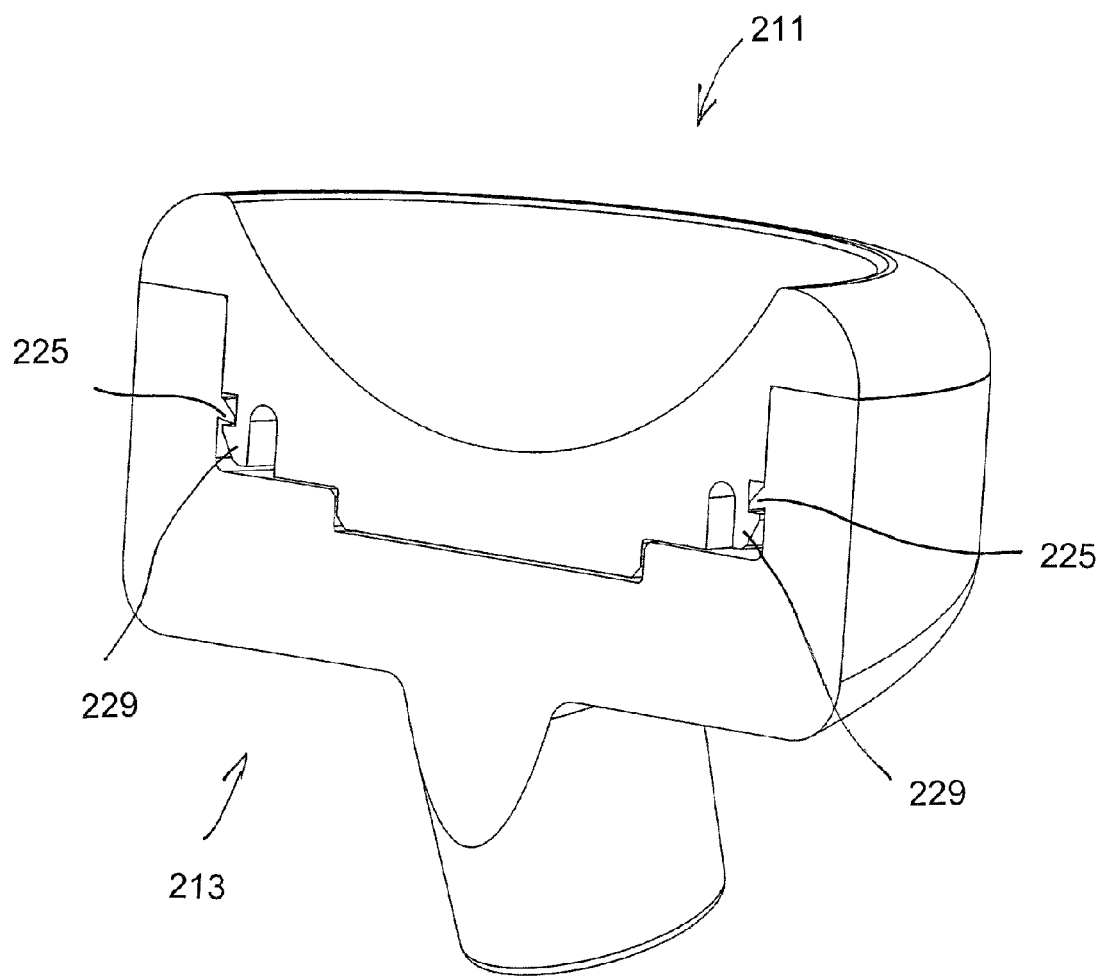

FIGS. 2 to 5, 12 show a shell, FIGS. 6 to 11, 13 an insert, and FIGS. 14, 15 a joint ball mount.

The shell 13 in accordance with FIGS. 2 to 5 has a conically converging spigot 39 with which the shell 13 can be anchored to a humerus shaft, not shown, or to the shoulder blade, optionally with a platform arranged therebetween. The outer cross-sectional shape of the conical spigot 39 is elliptic. The shell 13 has at its side provided for the mounting of the insert 11 described in the following with reference to FIGS. 6 to 11 a cylindrical section 41 in the form of a peripheral wall whose center axis 43 in accordance with FIG. 4 is inclined with respect to a center axis of the conical spigot 39. The cylindrical section 41 is interrupted at two mutually diametrically opposed points. The cut-outs 35 arising in this manner serve for the reception of corresponding projections 37 of the insert 11 in accordance with FIG. 6. A security against rotation of the insert 11 coupled to the shell 13 is hereby achieved. The inner side of the cylindrical peripheral wall 41 serves as a cylindrical inner guide region 33 for a corresponding cylindrical guide region 27 of the insert 11 in accordance with FIG. 6. At the "base" of the mount, a further cylindrical recess (without reference numeral) can be recognized which, as can be recognized in FIGS. 14 and 15, is provided for the reception of a second guide of the insert.

Figure 1A:
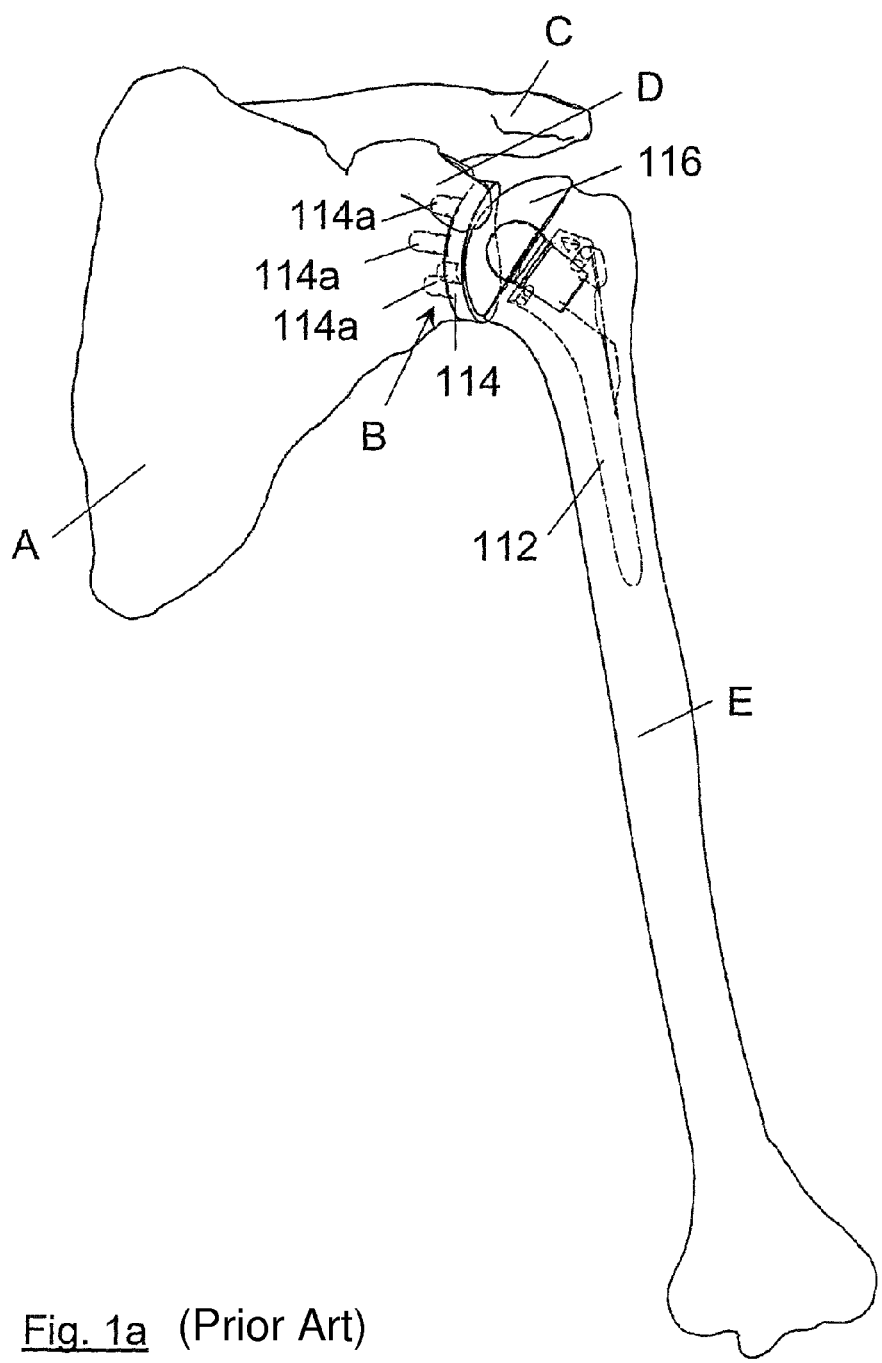
FIG. 1a is an elevational view of a shoulder joint including an anatomical prosthesis.
Figure 1B:
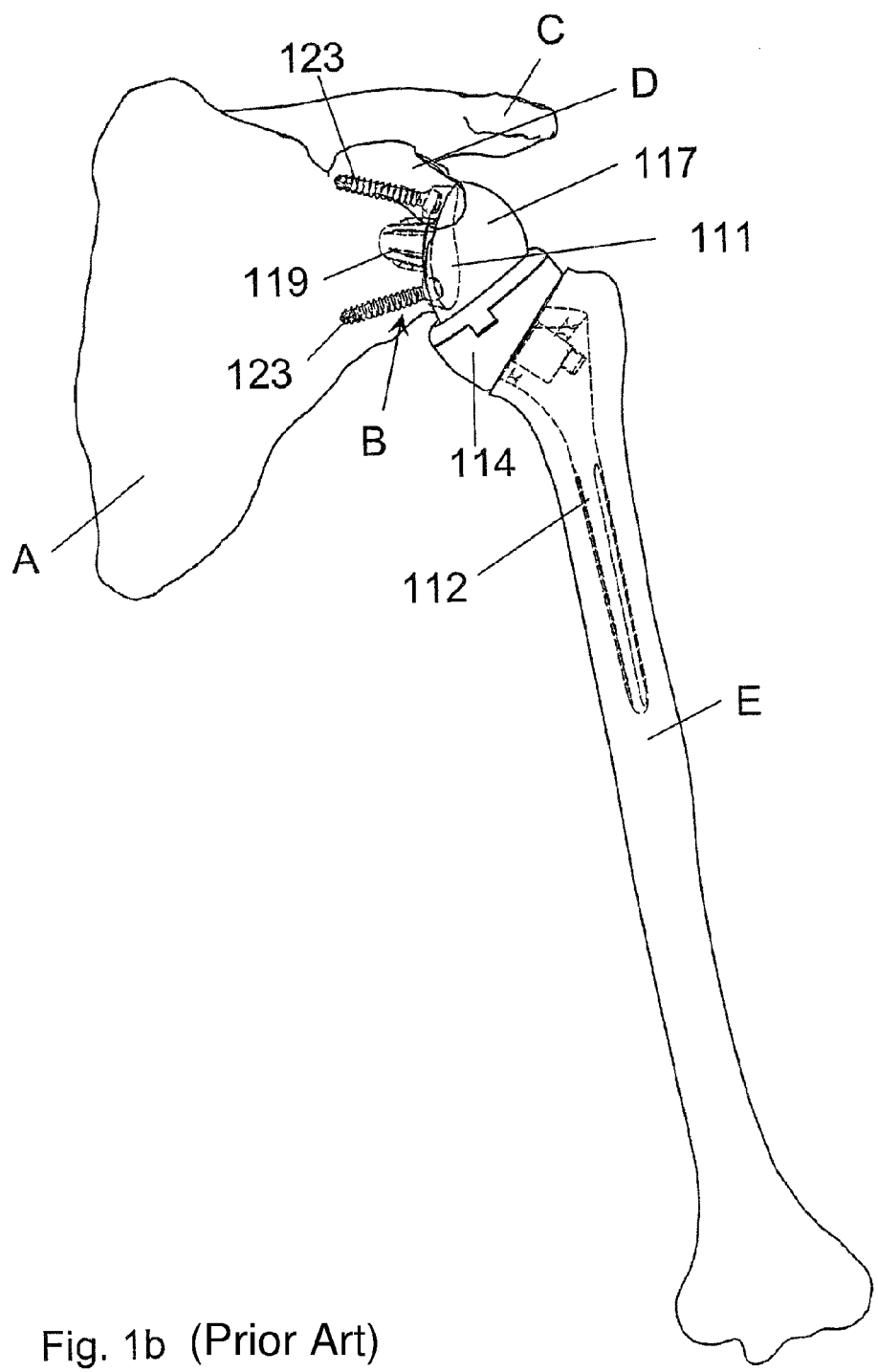
FIG. 1b is an elevational view of the shoulder joint including an inverse shoulder prosthesis.
Figure 1C:
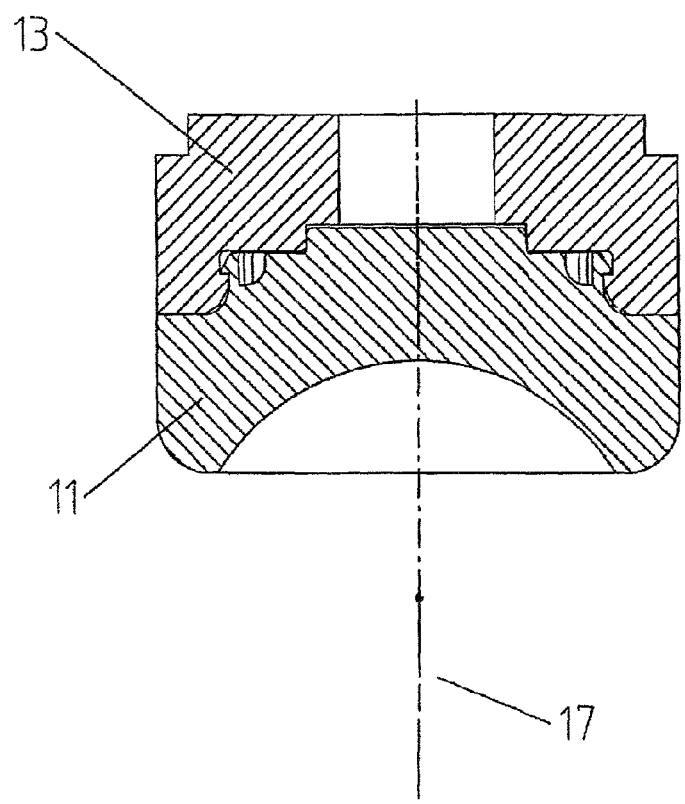
FIG. 1c is a sectional view of an insert in a shell of a prosthetic ball mount.
Figure 2:
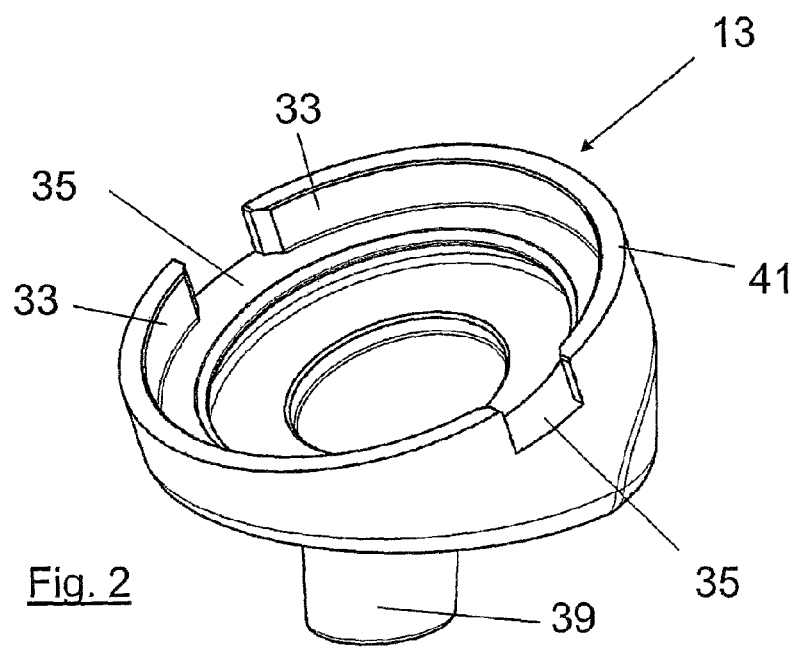
FIG. 2 is a perspective view of a prosthetic shell useable in a prosthetic ball mount.
Figure 3:
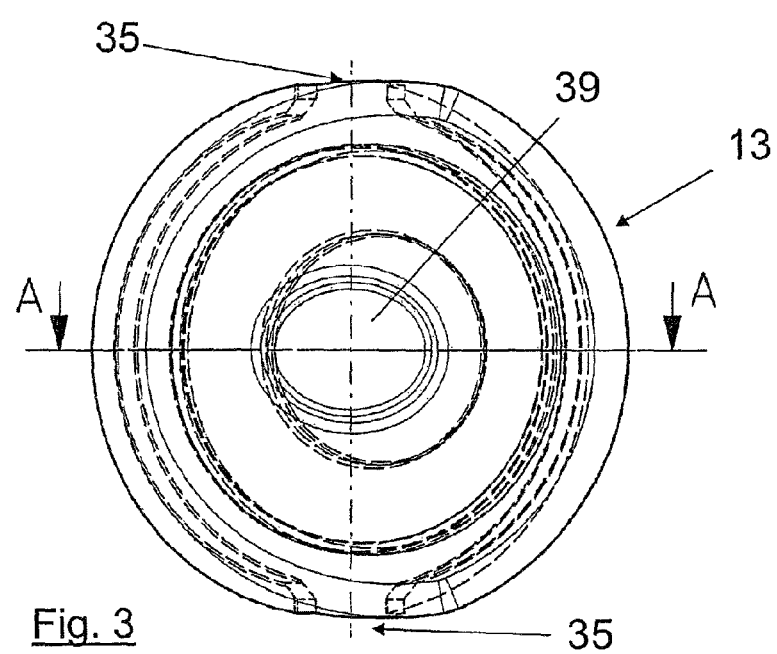
FIG. 3 is an elevational view of the prosthetic shell of FIG. 2.
Figure 6:
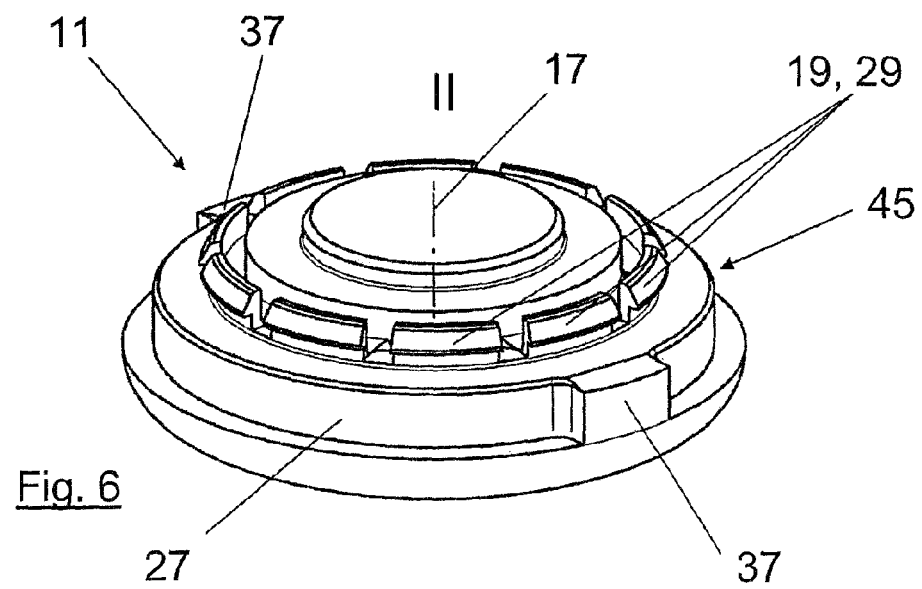
FIG. 6 is a perspective view of an insert adapted for cooperation with the prosthetic shell illustrated in FIGS. 2-5.
Figure 7:
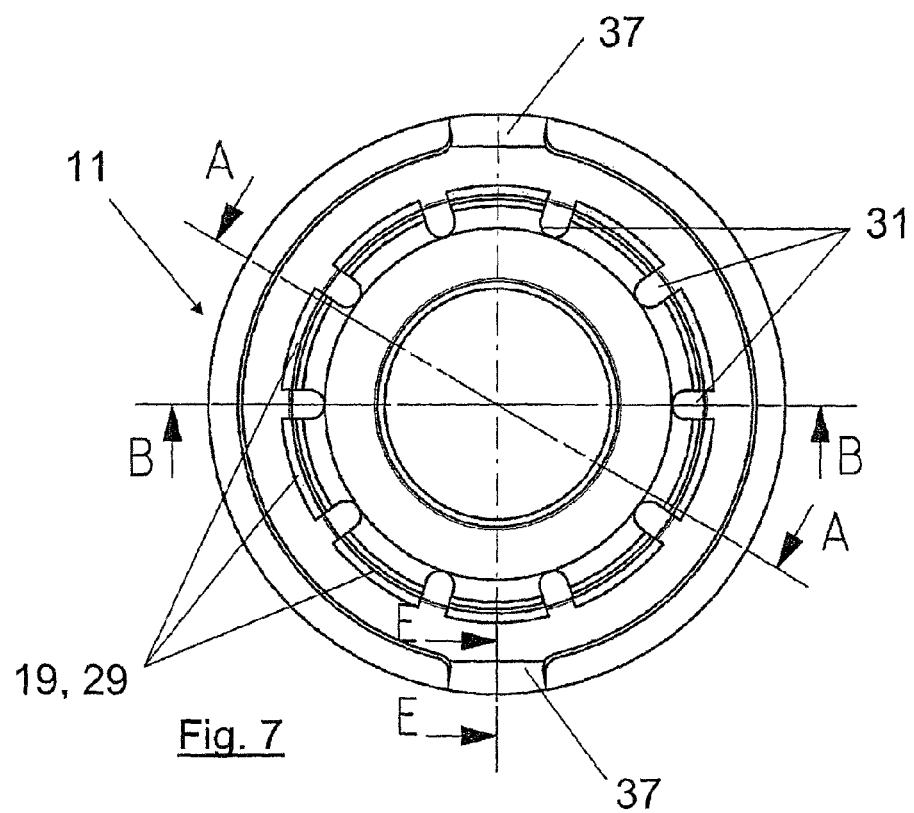
FIG. 7 is an elevational view of the insert of FIG. 6.
Figure 10:
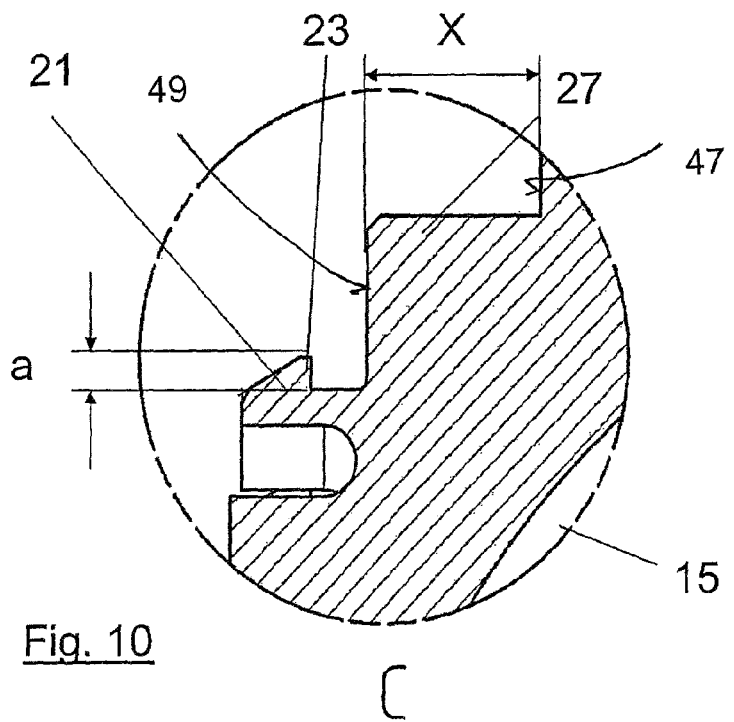
FIG. 10 is a partial detailed view of the cross-sectional view of FIG. 8.
Figure 11:
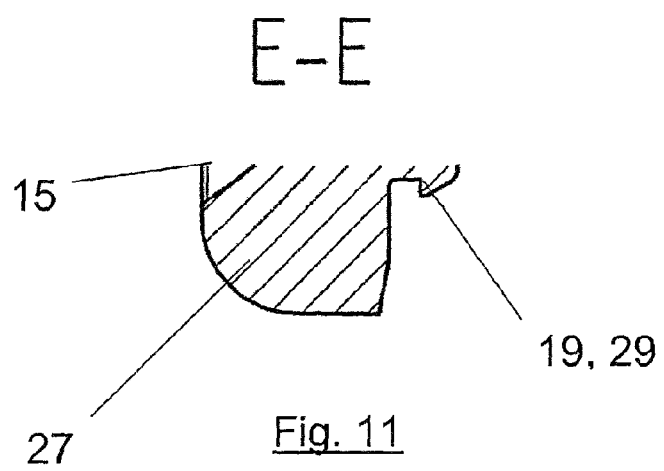
FIG. 11 is a partial cross-sectional view of the insert of FIG. 6 taken along line E-E of FIG. 7.

In FIG. 3, which shows a view of the shell 13 from "below" in accordance with FIG. 2, that is from its anchorage side, in particular the elliptical outer cross-sectional shape of the conical spigot 39 can be recognized.

It can in particular be seen from FIG. 4, which shows a section along the line "A-A" of FIG. 3, and from FIG. 5, which shows the detail "B" of FIG. 4, that the mount side of the shell 13 for the insert 11 is substantially formed by two cylindrical regions with different inner diameters. The region with a larger inner diameter is bounded by the already mentioned cylindrical inner guide region 33 and is separated from the region with a smaller inner diameter by a radially inwardly projecting peripheral projection which provides an undercut and serves as a counter-element 25 for a snap-action mechanism 19 of the insert 11 described in more detail in the following, see FIG. 6.

The insert 11 shown in FIGS. 6 to 11 is provided with a peripheral cylinder section 45 which has a cylindrical guide region 27 at its outer side which extends parallel to the center axis 17 of the insert 11, said center axis coinciding with the center axis of the cylinder section 45. The cylinder section 45 of the insert 11 is dimensioned in accordance with the mount region with a larger inner diameter of the shell 13 so that, in the assembled state, the cylindrical guide region 27 of the insert 11 and the cylindrical inner guide region 33 of the shell 13 are mutually oppositely disposed and cooperate, as described above. The dimensions are selected such that the insert 11 is inserted into the shell 13 with a small tolerance. The diameter tolerances are in particular dimensioned here such that the cylindrical guide region of the insert can be introduced into the shell without excessive force exertion and, on the other hand, a good centration and guidance is ensured. In a possible embodiment, the diameter of the cylindrical inner guide region 33 of the shell 13 can have an excess dimension with respect to the diameter of the cylindrical guide region 27 of the insert 11 of a maximum of 1/10 mm, or a maximum of 1%, for example less than 0.4%, of the diameter of the cylindrical guide region 27 of the insert 11. As is in particular shown in FIG. 10, the one axial end of the cylindrical guide region 27 adjoins, via a first ring-shaped surface 47 extending perpendicular to the axis of the cylindrical guide region 27, a section 53 of the insert 11 which is formed in the region of the first side I, see FIGS. 8 and 9, and at which this insert 11 has its maximum outer diameter, with the first ring-shaped surface 47 extending radially outwardly from the cylindrical guide region 27 such that the outer diameter of the cylindrical guide region 27 corresponds to the inner diameter of the first ring-shaped surface 47. The section 53 of the insert 11 is arranged outside the shell 13 in the condition coupled to the shell 13 such that the outer diameter of the cylindrical guide region 27 forms the largest diameter of the insert 11 disposed inside the shell 13 in the condition coupled with the shell 13. With its other end, the cylindrical guide region 27 adjoins the snap-action mechanism 19 of the insert 11 described in more detail below via a second ring-shaped surface 49 extending perpendicular to the axis of the cylindrical guide region 27, with the second ring-shaped surface 49 extending radially inwardly away from the cylindrical guide region 27 such that the outer diameter of the cylindrical guide region 27 corresponds to the outer diameter of the second ring-shaped surface 49. One of the two ring-shaped surfaces 47 or 49 acts in this connection as an axial abutment for a correspondingly formed counter-surface of the shell 13. A plurality of snap-action elements 29 of the insert 11 which are each made as a hook-like peripheral segment and are arranged radially inside the cylindrical guide region 27 cooperate with the counter-element 25 of the shell 13. The snap-action elements 29 are arranged uniformly distributed in the peripheral direction, with in each case an interruption 31 being present between two adjacent snap-action elements 29. In a possible embodiment, the interruptions 31 can each have a width of at least 1 mm. The interruptions 31 extend in each case in the axial direction from the end face of the cylinder section 45 extending perpendicular to the center axis 17 up to the free axial end of the snap-action elements 29. The totality of the snap-action elements 29 form a snap-action mechanism 19 in the form of a peripheral, interrupted collar 21 with an undercut 23, see FIG. 10, with the maximum outer diameter of the snap-action mechanism 19 being smaller than the outer diameter of the cylindrical guide region 27 which is arranged closer to the first side I than the snap-action mechanism 19. The projections 37 of the insert 11 which project radially with respect to the cylinder section 45 and are mutually diametrically oppositely disposed cooperate with the cut-outs 35 of the shell 13 in order—as already mentioned above—to hold the insert 11 with rotational security in the shell 13 in the coupled state. The snap-action mechanism 19 of the insert 11 is formed on a second side II of the insert 11 facing the shell 13 in the assembled state, whereas—as in particular FIGS. 8 and 9 show—a recess 15 is formed on the oppositely disposed first side I of the insert 11, said recess forming the actual mount for the joint ball of the prosthesis not shown here. Furthermore, a second guide region (without reference numeral) is arranged at the axial end of the second side II and can cooperate with a corresponding mount of the shell.

The following statements are made with respect to FIGS. 8 and 9. The recess 15 is made in the shape of a conical section and has a spherical surface region 51 which extends with respect to a center point M of the spherical surface region over an angular region $\Omega$ of, for example, 110°, i.e. over a semi-angular region $\Omega/2$ of, for example, 55°. The angle $\Omega$ in particular does not exceed an angle of 120° with shoulder joint support shells. In other embodiments, $\Omega$ is limited to maximum values of 110° or even 100° or 90°, in particular not to restrict the movability range of the shoulder joint and because a seating and the centration of the joint ball anyway takes place to a high degree by the ligament and muscular apparatus in shoulder joints; this in comparison, for example, with hip joints where a comparable rim width angle of the support shell comes in the order of magnitude of 180°. The recess 15 furthermore has a pole 55 which is disposed on the point of intersection of the center axis 17 with the spherical surface region 51, with the axial position of the axial end of the cylindrical second side guide region 27 facing the second side II being slightly offset, for example by 0.5 mm, with respect to the axial position of the pole 55 in the direction of the first side I.

It is generally also possible for the axial position of the axial end of the cylindrical guide region 27 facing the second side II to be slightly offset in the direction of the second side II. The axial end of the cylindrical guide region 27 facing the second side II can therefore also be arranged "lower" than the pole 55 of the recess 15—considered from the first side I. FIG. 9 furthermore shows a gradient angle $\omega$ which is formed between a perpendicular 57 to the center axis 17 and a tangent 59 at the spherical surface region 51. The tangent 59 is applied at an axial position of the spherical surface region 51 which corresponds to the axial position of the end of the cylindrical guide region 27 facing the first side I.

The gradient angle $\omega$ amounts in the embodiment shown, for example, to less than 45° and can amount to the angle $\Omega/2$. Other gradient angles, which are present at axial positions at the spherical surface region 51, which correspond to the axial positions of other regions of the cylindrical guide regions 27, are consequently disposed in the range between 0° and the gradient angle $\omega$ which corresponds to the axial position of the end of the cylindrical guide region 27 facing the first side I. It can furthermore be seen from FIG. 10 that the axial extent x of the cylinder section 45, and thus of the cylindrical guide region 27 of the insert 11, amounts to a multiple of the depth a of the undercut 23 of the collar 21 formed by the snap-action elements 29 measured in the radial direction with respect to the center axis 17. In a possible embodiment, the depth a of the undercut amounts to at least 1 mm, for example more than 1.3 mm. With respect to the outer diameter of the snap-action mechanism 19, the depth a of the undercut 23 can amount in a possible embodiment to at least 3%, at least 3.5% in an embodiment, of this outer diameter. The axial extent x of the cylindrical guide region 27 parallel to the center axis 17 of the insert 11 can amount to at least 3 mm, in particular to at least 3.5 mm. With respect to the outer diameter of the cylindrical guide region 27, its axial extent x parallel to the center axis 17 can amount to at least 10% of this outer diameter. As regards the axial extent of the cylindrical inner guide region 33 of the shell 13, this is at least substantially just as large in an embodiment as the axial extent x of the cylindrical guide region 27 of the insert 11 to be received.

In a further embodiment in accordance with the FIGS. 12 and 13, a security against rotation is provided whose components, cut-out and projection, are particularly swapped over with respect to their arrangement at the shell and insert with respect to the security against rotation explained in connection with the embodiment in accordance with FIGS. 2 to 11. The shell 213 shown in FIG. 12 includes a cylinder section 241 which has a respective radially inwardly projecting projection 237 at two mutually diametrically opposed points. The projections 237 are received in the assembled state by corresponding cut-outs 235 of the insert 211 which are provided at two mutually diametrically opposed points in a cylinder section 245 of the insert 211. Otherwise, the embodiment in accordance with FIGS. 12 and 13 corresponds to the embodiment in accordance with FIGS. 2 to 11, with aspects already explained in the above again being taken up or repeated in the following with respect to FIGS. 14 and 15.

In FIGS. 14 and 15, a longitudinal section is shown through a joint ball mount made up of the shell 213 in accordance with FIG. 12 and the insert 211 in accordance with FIG. 13 along the center axis of the insert 211 or of the center axis of the cylinder section 241 of the shell 213. The cylinder section 245 of the insert 211 has a cylindrical guide region 227 at its outer side which cooperates with a cylindrical inner guide region 233 of the cylinder section 241 of the shell 233 such that a full-area mutual contact of the cylinder sections 241 and 245 is realized. The insert 211 furthermore has a plurality of undercut, elastically deformable snap-action elements 229 which engage behind a peripheral projection 225 of the shell 213 so that a snap-in connection is formed between the insert 211 and the shell 213.

The insert 11 shown in the Figures is made of plastic in one embodiment, in particular of polyethylene. The minimal material thickness of the supporting region, adjacent to the recess 15 provided for the reception of the joint ball, amounts, for example to not less than 3 mm and lies in specific embodiments at 3.4 mm to 4.0 mm, more specifically at 3.5 mm, at most in a tolerance range of ±0.5 mm. The material thickness is measured in this context in the radial direction of the ball-shaped or sphere-shaped recess 15 for the reception of the joint ball, that is in the direction of the surface normal force introduction.

The joint ball mount 11, 13 described here can be fastened conventionally—in a configuration also called "anatomical"—to the scapula. The described components are also very well suited for the formation of a shoulder joint prosthesis in which the joint ball mount 11, 13 is provided—in a configuration also called "inverse"—for fastening to the humerus. In this context, the joint ball mount 11, 13 is fastened, for example, to a shaft known per se such as is used for fastening in a long bone and which can be anchored easily in the humerus—cemented or not cemented depending on the embodiment.

The invention claimed is:
1. An insert of a joint ball mount of a shoulder joint prosthesis, the insert comprising:
a first side having a recess sized to receive a joint ball;
a second side opposite the first side;

a snap-action mechanism extending around a center axis of the insert, the snap-action mechanism comprising:
  a collar arranged proximate the second side; and
  an undercut extending around the center axis,
    wherein the snap-action mechanism includes at least one radial interruption in the collar;
a first cylindrical guide region disposed at an outer periphery of the insert and configured to interface with a first cylindrical inner shell guide region,
  wherein an outer diameter of the first cylindrical guide region is larger than a maximum outer diameter of the snap-action mechanism and smaller than a maximum outer diameter of the insert, and
  wherein the first cylindrical guide region is arranged between the first side and the snap-action mechanism; and
a second cylindrical guide region proximate the second side of the insert and configured to interface with a second inner shell guide region wherein an outer diameter of the second cylindrical guide region is smaller than the outer diameter of the first cylindrical guide region and the maximum outer diameter of the snap-action mechanism such that the snap-action mechanism is arranged axially between the first and second cylindrical guide regions.

2. An insert in accordance with claim 1, wherein a central axis defined by the first cylindrical guide region coincides with the center axis of the insert.

3. An insert in accordance with claim 1, wherein the maximum outer diameter of the insert is disposed at the first side and adjoined by the first cylindrical guide region after a step-like diameter reduction.

4. An insert in accordance with claim 1, wherein the first cylindrical guide region includes means for preventing rotation of the insert.

5. An insert in accordance with claim 1, in combination with a shell sized to receive a portion of the insert within the shell to couple the shell and the insert, wherein:
  the outer diameter of the first cylindrical guide region is the largest diameter of the portion of the insert received within the shell when the shell and insert are coupled, and
  the first side of the insert defining an articular surface extending axially outside of the shell when the shell and the insert are coupled.

6. A combination in accordance with claim 5, wherein the maximum outer diameter of the insert is commensurate with a maximum outer diameter of the shell.

7. An insert in accordance with claim 1, wherein the first cylindrical guide region defines a first ring-shaped surface, the second cylindrical guide region defines a second ring-shaped surface, the second ring-shaped surface defining an axial abutment surface, each ring-shaped surface disposed at respective axial ends of the first and second cylindrical guide regions, the first and second ring-shaped surfaces each extending transversely to respective axes of the first and second cylindrical guide regions.

8. An insert in accordance with claim 1, wherein the recess has a spherical surface region which extends over an angular range of less than or equal to 120° with respect to a center of the spherical surface region.

9. An insert in accordance with claim 1, wherein the recess has a spherical surface region, an axial end of the first cylindrical guide region proximate the first side defining an axial position, a tangent to the spherical surface region taken at the axial position defining a gradient angle with a line perpendicular to the center axis of the insert, the gradient angle less than 60°.

10. An insert in accordance with claim 1, wherein an end of the first cylindrical guide region toward the second side of the insert defines a first axial position along the center axis, a pole of the recess defining a second axial position along the center axis, said first axial position disposed proximate the second axial position.

11. An insert in accordance with claim 10, wherein the first axial position is offset less than 2 mm from the second axial position.

12. An insert in accordance with claim 1, wherein an axial extent of the first cylindrical guide region is at least 3 mm.

13. An insert in accordance with claim 1, wherein an axial extent of the first cylindrical guide region is at least 10% of the outer diameter of the first cylindrical guide region.

14. An insert in accordance with claim 1, wherein the snap-action mechanism includes a plurality of interruptions uniformly distributed about a periphery of the collar of the snap-action mechanism.

15. An insert in accordance with claim 1, wherein the snap-action mechanism is divided into at least two peripheral segments which are separate from one another, with there being a gap-shaped interruption of a width of at least 1 mm between two respective adjacent peripheral segments.

16. An insert in accordance with claim 1, wherein a depth of the undercut of the snap-action mechanism is at least 1 mm.

17. An insert in accordance with claim 1, wherein a depth of the undercut of the snap-action mechanism is at least 3% of the maximum outer diameter of the snap-action mechanism.

18. An insert in accordance with claim 1, in combination with a shell of a joint ball mount of a shoulder joint prosthesis for mounting of the insert wherein the shell comprises:
  the first cylindrical inner shell guide region disposed at an inner side of the shell, the first cylindrical inner shell guide region sized to receive the first cylindrical guide region of the insert, and
  the second inner shell guide region disposed at a base opening formed in the mount, the second shell guide region sized to receive the second cylindrical guide region of the insert.

19. An insert in accordance with claim 18, wherein a diameter of the first cylindrical inner shell guide region is larger than the diameter of the first cylindrical guide region of the insert by one chosen from a maximum of $\frac{1}{10}$mm, and a maximum of 1% of the diameter of the first cylindrical guide region of the insert.

20. An insert in accordance with claim 18, wherein an axial extent of the first cylindrical inner shell guide region is at least as large as an axial extent of the first cylindrical guide region of the insert.

21. An insert of a shoulder joint prosthesis in accordance with claim 18, wherein the shell is adapted to be fastened to a humerus to articulate with a ball component, whereby the joint ball mount is configured as an inverse shoulder joint prosthesis.

22. An insert in accordance with claim 18, wherein the insert includes at least one anti-rotation projection projecting radially outwardly from the insert, and the shell includes at least one cut-out sized and positioned to receive the anti-rotation projection of the insert when the insert is received within the shell, cooperation between the projection and cut-out preventing rotation of the insert relative to the shell when the insert is received within the shell.

23. An insert in accordance with claim 18, wherein the shell further comprises a peripheral projection disposed between the first and second inner shell guide regions, the peripheral projection extending radially inwardly toward a central shell axis and positioned to engage the snap-action mechanism of the insert when the insert is received within the shell, engagement between the snap-action mechanism axially fixing the insert to the shell.

24. An insert in accordance with claim 23, wherein the peripheral projection formed in the shell defines a ring-shaped face facing toward the second inner shell guide region.

25. An insert in accordance with claim 1, wherein the first side has a rounded outer periphery adjacent to the recess sized to receive the joint ball, the rounded outer periphery shaped to be disposed outside of a corresponding shell component upon implantation.

26. A socket component of a joint prosthesis, the socket component adapted to articulate with a ball component to form a ball-and-socket prosthesis, the socket component comprising:
   a shell having a bone anchoring side and an insert mounting side disposed along a central shell axis, the shell comprising a cavity formed in the insert mounting side, the cavity comprising:
      a first shell guide region facing inwardly toward the shell axis, the first shell guide region having a first shell guide region diameter;
      a second shell guide region facing inwardly toward the shell axis, the second shell guide region having a second shell guide region diameter that is smaller than the first shell guide region diameter;
   an insert having a mounting side and a recess side disposed along a central insert axis, the recess side defining a maximum outer diameter of the insert, the recess side sized to receive the ball component, the insert comprising:
      a first insert cylindrical guide region facing outwardly away from the shell axis, the first insert cylindrical guide region having a first insert guide region diameter that is smaller than the first shell guide region diameter, whereby the first insert guide region is sized to interface with and fit within the first shell guide region;
      a second insert cylindrical guide region facing outwardly away from the shell axis, the second insert cylindrical guide region having a second insert guide region diameter that is smaller than the second shell guide region diameter, whereby the second insert guide region is sized to interface with and fit within the second shell guide region, an outer diameter of the first insert guide region smaller than the maximum outer diameter of the insert; and
   means for coupling the insert in fixed engagement with the shell when the first and second insert guide regions are interfacing and fit within the first and second shell guide regions, respectively, a portion of the recess side of the insert disposed outside of the cavity of the shell when the insert is coupled in fixed engagement with the shell.

27. The socket component of claim 26, wherein the means for coupling the insert comprise:
   a peripheral projection formed in the shell and disposed between the first shell guide region and the second shell guide region, the peripheral projection extending radially inwardly toward the central shell axis; and
   a snap-action mechanism monolithically formed in the insert and disposed between the first insert guide region and the second insert guide region, the snap-action mechanism projecting radially outwardly away from the central insert axis.

28. The socket component of claim 26, wherein the maximum outer diameter defined by the recess side of the insert is equal to a maximum outer diameter of the insert mounting side of the shell, such that the insert and the shell cooperate to define the outer peripheral surface of the socket component when the insert is coupled in fixed engagement with the shell.

* * * * *

UNITED STATES PATENT AND TRADEMARK OFFICE
CERTIFICATE OF CORRECTION

PATENT NO. : 8,608,805 B2
APPLICATION NO. : 12/066948
DATED : December 17, 2013
INVENTOR(S) : Forrer et al.

It is certified that error appears in the above-identified patent and that said Letters Patent is hereby corrected as shown below:

On the Title Page

In column 1, under Item "(75) Inventors", line 3, delete "Constance" and insert --Konstanz--, therefor In column 2, under Item "(57) Abstract", line 6, delete "snap action" and insert --snap-action--, therefor In column 2, under Item "(57) Abstract", line 14, after "(11)", delete "at", therefor On page 3, in column 2, under "Other Publications", line 5, delete ""Reverse"Total" and insert --"Reverse" Total--, therefor In the Claims In column 7, line 20, in Claim 1, after "region", insert --,--, therefor In column 8, line 3, in Claim 9, delete "60° ." and insert --60°.--, therefor In column 8, line 46, in Claim 19, delete "$^1/_{10}$mm," and insert --1/10 mm,--, therefor Signed and Sealed this
Fifteenth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,608,805 B2                                   Page 1 of 1
APPLICATION NO. : 12/066948
DATED            : December 17, 2013
INVENTOR(S)      : Forrer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 102 days.

Signed and Sealed this
Twenty-second Day of September, 2015

Michelle K. Lee
*Director of the United States Patent and Trademark Office*